(12) United States Patent
Kobayashi et al.

(10) Patent No.: US 10,194,489 B2
(45) Date of Patent: Jan. 29, 2019

(54) ELECTRIC HEATER AND METHOD FOR MANUFACTURING ELECTRIC HEATER

(71) Applicant: YOSHINOGAWA ELECTRIC WIRE & CABLE CO., LTD., Takamatsu-shi, Kagawa (JP)

(72) Inventors: Shigeru Kobayashi, Takamatsu (JP); Kazuo Hira, Takamatsu (JP)

(73) Assignee: YOSHINOGAWA ELECTRIC WIRE & CABLE CO., LTD., Takamatsu-shi, Kagawa (JP)

( * ) Notice: Subject to any disclaimer, the term of this patent is extended or adjusted under 35 U.S.C. 154(b) by 568 days.

(21) Appl. No.: 14/778,913

(22) PCT Filed: Mar. 20, 2014

(86) PCT No.: PCT/JP2014/057657
§ 371 (c)(1),
(2) Date: Oct. 20, 2015

(87) PCT Pub. No.: WO2014/148590
PCT Pub. Date: Sep. 25, 2014

(65) Prior Publication Data
US 2016/0050719 A1 Feb. 18, 2016

(30) Foreign Application Priority Data
Mar. 22, 2013 (JP) .................. 2013-060217

(51) Int. Cl.
*H05B 3/44* (2006.01)
*A61B 18/08* (2006.01)
(Continued)

(52) U.S. Cl.
CPC ............. *H05B 3/44* (2013.01); *A61B 18/082* (2013.01); *H01C 17/02* (2013.01); *H05B 3/0014* (2013.01);
(Continued)

(58) Field of Classification Search
CPC .......... H05B 3/44; H05B 3/0014; H05B 3/48; H05B 3/52; A61B 18/082;
(Continued)

(56) References Cited

U.S. PATENT DOCUMENTS 3,698,394 A 10/1972 Piper et al.
4,723,066 A 2/1988 Kurokawa et al.
(Continued)

FOREIGN PATENT DOCUMENTS

DE 3518245 A1 11/1986
EP 0132276 A1 1/1985
(Continued)

OTHER PUBLICATIONS

Machine Translation: Hara et al (JP 2010-205680) published 2010, machine translation performed Feb. 2018.*
(Continued)

*Primary Examiner* — Brian W Jennison
(74) *Attorney, Agent, or Firm* — Muncy, Geissler, Olds & Lowe, P.C.

(57) ABSTRACT

An electric heater 1 comprising a linear heater body 20 accommodated in a heat transfer tube 10, wherein a bent-back part 24 of the heater body 20 is formed inside the heat transfer tube 10 such that a pair of ends 26a and 26b emerge from a first-end side of the heat transfer tube 10, and the heater body 20 comprises a heating part 25 formed so as to extend along a part of the heat transfer tube 10 and a lead part 26 capable of electrically connecting the heating part 25 to the outside of the heat transfer tube 10. The electric heater 1 can be inserted into a narrow space and perform topical heating.

17 Claims, 3 Drawing Sheets

(51) Int. Cl.
*H01C 17/02* (2006.01)
*H05B 3/00* (2006.01)
*H05B 3/48* (2006.01)
*H05B 3/52* (2006.01)
*A61B 18/00* (2006.01)

(52) U.S. Cl.
CPC ............... *H05B 3/48* (2013.01); *H05B 3/52* (2013.01); *A61B 2018/00071* (2013.01); *A61B 2018/00083* (2013.01); *A61B 2018/00089* (2013.01); *A61B 2018/00107* (2013.01); *A61B 2018/00595* (2013.01); *A61B 2018/00821* (2013.01)

(58) Field of Classification Search
CPC .. A61B 2018/00071; A61B 2018/0083; A61B 2018/00089; A61B 2018/00107; A61B 2018/00595; A61B 2018/00821
USPC ........................................................ 219/534
See application file for complete search history.

(56) References Cited

U.S. PATENT DOCUMENTS

| | | |
|---|---|---|
| 2008/0167643 A1 | 7/2008 | Mizrahi et al. |
| 2009/0260852 A1 | 10/2009 | Schaffer |
| 2010/0268208 A1* | 10/2010 | Manwaring .......... A61B 18/082 606/30 |

FOREIGN PATENT DOCUMENTS

| | | |
|---|---|---|
| JP | S57-34847 A | 2/1982 |
| JP | 1987-031892 U | 2/1987 |
| JP | 2010-205680 A | 9/2010 |
| JP | 5068662 B2 | 11/2012 |

OTHER PUBLICATIONS

Supplementary European Search Report dated Nov. 17, 2016 in corresponding EP patent application No. 14768654.
International Search Report of PCT/JP2014/057657.

* cited by examiner

ELECTRIC HEATER AND METHOD FOR MANUFACTURING ELECTRIC HEATER

TECHNICAL FIELD

The present invention relates to an electric heater and a manufacturing method therefor, and, more specifically, relates to an electric heater suitable for being accommodated in a small space such as the interior of a puncture needle for puncturing a living body, and a manufacturing method therefor.

BACKGROUND ART

Electric heaters have been used in various applications for heating, and retaining the heat of, various devices, components, etc. Recently, research has been conducted into the use of an electric heater in a therapeutic method for thermally cauterizing a diseased site, and a thin electric heater usable in such an application is desired. For example, the electrically heated needle disclosed in Patent Literature 1 is configured such that a heating element and a thermocouple are accommodated in a hollow pipe, the distal end of which is blocked by a chip capable of puncturing a living body. The heating element is formed by winding a fine heating wire in a coil-like manner around a core composed of a thread of glass fiber, with the distal side to be inserted into the hollow pipe being half-folded, and the proximal side being connected to a covered electrical wire via a connector.

CITATION LIST

Patent Literature

Patent Literature 1: JP 2010-205680A

SUMMARY OF INVENTION

Technical Problem

The above-described conventional electrically heated needle achieves a reduced heating element diameter, but, on the other hand, since the heating element and the covered electric wire are connected via a connector provided outside the hollow pipe, attempts to ensure a hollow pipe length necessary for puncture inevitably result in an increased length of the heating element. Therefore, there is a problem that it is difficult to topically heat only the vicinity of a diseased site in an efficient manner.

Accordingly, an object of the present invention is to provide an electric heater that can be inserted into a narrow space and perform topical heating, and a manufacturing method therefor.

Solution to Problem

The foregoing object of the present invention is achieved by an electric heater comprising a linear heater body accommodated in a heat transfer tube, wherein a bent-back part of the heater body is formed inside the heat transfer tube such that a pair of ends emerge from a first-end side of the heat transfer tube, and the heater body comprises a heating part formed so as to extend along a part of the heat transfer tube and a lead part capable of electrically connecting the heating part to the outside of the heat transfer tube.

In this electric heater, a portion of the heater body, where a surface of a linear body composed of a metal material having a high electrical resistivity is partially covered with a covering composed of a metal material having a lower electrical resistivity than the material of the linear body, can be the lead part, and a portion where the linear body is exposed can be the heating part. The bent-back part is preferably formed in the heating part.

It is preferable that the heating part is covered with a jacket and is at least partially in contact with an inner circumferential surface of the heat transfer tube via the jacket. In this configuration, a ratio of a length in an axial direction of a portion of the heating part in contact with the heat transfer tube to a total length of the heating part is preferably 0.1 to 1. Moreover, it is preferable that the heating part is in contact with multiple places of the heat transfer tube, or it is preferable that the heating part is in contact with both sides of the heat transfer tube across the bent-back part.

It is preferable that the heating part is composed of a shape-memory alloy or a high-tension wire rod.

It is preferable that both ends of the heat transfer tube are open, and it is preferable that the heat transfer tube is filled with a sealing resin.

It is preferable that the sealing resin is an epoxy resin.

It is preferable that the heat transfer tube has an outer diameter of 0.2 to 0.7 mm.

It is preferable that a gap formed between the heating part and the heat transfer tube has an average of 0 to 0.1 mm.

It is preferable that a ratio of resistances (R1/R2) is 20 or greater where R1 and R2 represent resistances per unit length in an axial direction of the linear body and the covering, respectively.

The heater body can be configured to comprise an inner conductor and an outer conductor coaxially disposed via an insulator, and configured such that the inner conductor and the outer conductor are made conductive at ends, whereby the bent-back part is formed. In this configuration, the heating part can be formed by configuring a part of the outer conductor to be a high-resistance part along an axial line.

It is preferable that any electric heater described above further comprises a temperature sensor for sensing a temperature near the heating part inside the heat transfer tube, and it is preferable that a temperature sensing part of the temperature sensor is in contact with an inner circumferential surface of the heat transfer tube.

Moreover, the foregoing object of the present invention is achieved by a method for manufacturing the electric heater described above, comprising:

a first step of producing the heater body by partially covering a surface of a linear body composed of a high-resistance metal material with a low-resistance metal material having a lower electrical resistivity than the material of the linear body and forming the bent-back part in the linear body; and a second step of accommodating the heater body in the heat transfer tube, wherein a portion where the linear body is covered with the low-resistance metal material constitutes the lead part, and a portion where the linear body is exposed constitutes the heating part.

In this electric heater manufacturing method, it is preferable that the heating part is formed from a high-tension wire rod and covered with a jacket, and it is preferable that the second step comprises firmly attaching the heating part to an inner circumferential surface of the heat transfer tube via the jacket by elastic force exerted when bending the heating part.

Alternatively, it is preferable that the heating part is formed from a shape-memory alloy and covered with a jacket, and it is preferable that the second step comprises firmly attaching the heating part to an inner circumferential surface of the heat transfer tube via the jacket by thermally deforming the heating part after the heating part is accommodated in the heat transfer tube.

Advantageous Effects of Invention

According to the present invention, an electric heater that can be inserted into a narrow space and perform topical heating, and a manufacturing method therefor, are provided.

DESCRIPTION OF EMBODIMENTS

Figure 1:
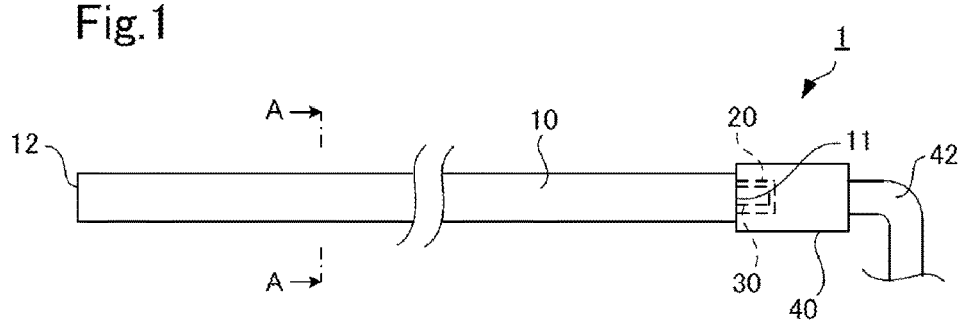
FIG. 1 is a plan view of an electric heater according to the first embodiment of the present invention.
Figure 2:
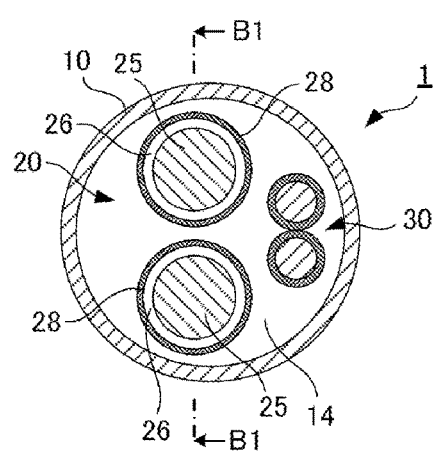
FIG. 2 is a cross-sectional view taken along the line A-A of FIG. 1.
Figure 3:
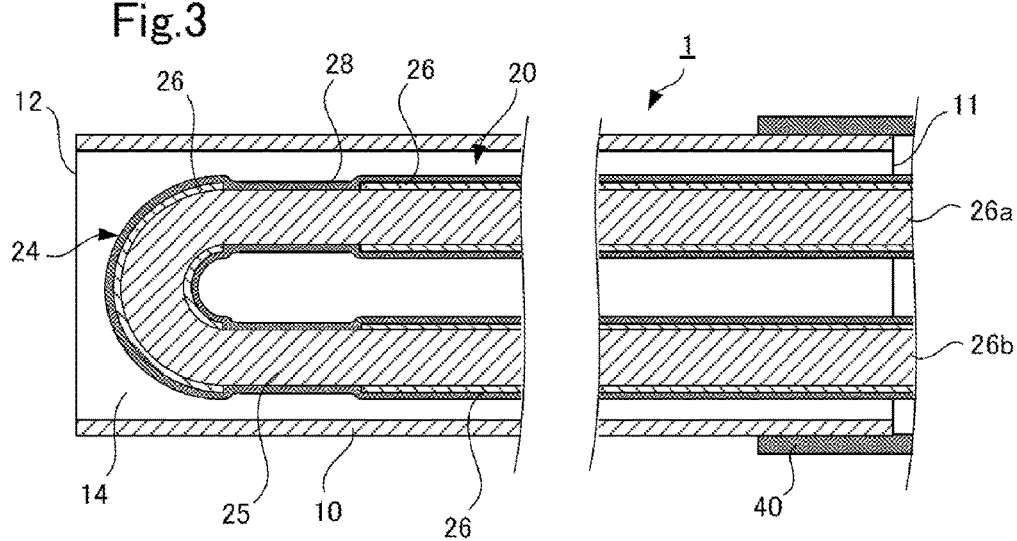
FIG. 3 is a cross-sectional view taken along the line B1-B1 of FIG. 2.

Below, an embodiment of the present invention will now be described with reference to the appended drawings. FIG. 1 is a plan view of an electric heater according to the first embodiment of the present invention, and FIGS. 2 and 3 are cross-sectional views taken along the lines A-A of FIG. 1 and B1-B1, respectively. As shown in FIGS. 1 to 3, an electric heater 1 is configured to accommodate a linear heater body 20 inside a heat transfer tube 10. The heat transfer tube 10 is formed from a material with good thermal conductivity (e.g., a metal material such as stainless steel or copper), and openings 11 and 12 are formed at the respective ends. The thickness of the heat transfer tube 10 is not particularly limited, and an extremely thin tube having an outer diameter of, for example, about 0.3 mm is usable. It is preferable that the heat transfer tube 10 is self-supporting and flexible so as to be easily inserted into a narrow space.

In the heater body 20, a heating part 25 and a lead part 26 are connected in the longitudinal direction, and a bent-back part 24 is formed by bending any part of the heating part 25 and the lead part 26. The heater body 20 can be produced by partially covering the surface of a linear body composed of a metal material having a high electrical resistivity with a metal plating film or a metal foil composed of a metal material having a lower electrical resistivity than the linear body, with the portion where the linear body is covered with a covering composed of a low-resistance metal material constituting the lead part 26 and the portion where the linear body is exposed constituting the heating part 25. Such a method for producing the heater body 20 makes it possible to easily and reliably form the heating part 25 and the lead part 26. The position of the heating part 25 in the heater body 20 is not particularly limited, and the heating part 25 may be formed not only in one place but multiple places, and, as will be described below, it is preferable that at least the bent-back part 24, which is the distal part of the heater body 20, is formed in the heating part 25 because the precise positioning of the heating part 25 inside a living body can be accomplished. The production of the heater body 20 is not limited to the above-described method, and, for example, the heater body can also be formed by disposing a heating part composed of a linear member between a plurality of lead parts composed of a cylindrical member and cramp-fixing the respective ends of the heating part to the open ends of the lead parts.

Examples of the high-resistance metal material of the linear body constituting the heating part 25 include nickel, iron, platinum, chromium, titanium, and alloys thereof (such as stainless steel and nichrome). Although the linear body is preferably a solid wire for providing a fine wire, the linear body may be composed of a strand of multiple solid wires. On the other hand, examples of the low-resistance metal material of the covering that covers the linear body to form the lead part 26 include gold, silver, copper, aluminum, and alloys thereof.

The heating part 25 and the lead part 26 are covered with a jacket 28. It is preferable that the jacket 28 has excellent heat conductivity, heat resistance, and electrical insulation, and a polyimide resin is used in the present embodiment. Other examples include fluororesins, olefin resins, polystyrene resins, polyester resins, polyurethane resins, ABS resins, polymer alloys of polyamide resins and ABS resins, and the like. The jacket 28 can be formed from a tube or a coating that covers the heating part 25 and the lead part 26. While an excessively large thickness of the jacket 28 results in poor heat conductivity, an excessively small thickness is likely to result in poor electrical insulation, and therefore the thickness is preferably about 0.5 to 10 μm.

In the heater body 20, a pair of ends 26a and 26b of the lead part 26 are disposed so as to emerge from an opening 11 on the first-end side of the heat transfer tube 10, and the bent-back part 24 is disposed near an opening 12 on the second-end side of the heat transfer tube 10. By inserting the heater body 20, with the bent-back part 24 being formed in advance, from the pair of ends 26a and 26b into the heat transfer tube 10 through the opening 12 on the second-end side and adjusting how much the heater body 20 emerges from the opening 11 on the first-end side, the positioning of the bent-back part 24 inside the heat transfer tube 10 can be easily accomplished. The pair of ends 26a and 26b of the heater body 20 are connected to a connecting cord 42 via a feeder wire (not shown) inside a sleeve 40 attached to the end of the heat transfer tube 10. The connecting cord 42 can be connected to, for example, a power unit, which is not shown. In this way, the heating part 25 can be electrically connected to the outside of the heat transfer tube 10 via the lead part 26.

Other than the heater body 20, a temperature sensor 30 such as a thermocouple is accommodated in the interior of the heat transfer tube 10. The temperature sensor 30 is inserted into the heat transfer tube 10 through the opening 11 on the first-end side, and the temperature sensing part (not shown) on the distal side is disposed near the heating part 25 of the heater body 20. The temperature sensor 30 is connected to the connecting cord 42 within the sleeve 40 as well. The temperature sensor 30 senses the temperature near the heating part 25, and thus power-supplying control for heating the heating target at a desired temperature can be precisely performed.

A gap formed between the inner surface of the heat transfer tube 10 and the surfaces of the heater body 20 and the temperature sensor 30 is filled with a sealing resin 14. It is preferable that the sealing resin 14 has good heat conductivity, and, for example, epoxy resins, imide resins, silicon resins, fluororesins, and the like can be suitably used. In particular, not only can epoxy resins be easily filled into the heat transfer tube 10 when those having a low viscosity are selected, but also epoxy resins can be suitably used as the sealing resin 14 because epoxy resins have good heat conductivity (about 10 times greater than air), have high heat resistance (an upper temperature limit of about 200° C.), and barely shrink during the course of curing. The heat conductivity of the sealing resin 14 can be further increased by adding an additive such as alumina or silica.

When the inner diameter of the heat transfer tube 10 is small, the gap of the heat transfer tube 10 can be filled with the sealing resin 14 by causing a low-viscosity resin solution to permeate the gap by taking advantage of capillarity and then solidifying the resin. Alternatively, the gap can be filled by pressure-injection of the sealing resin 14 into the heat transfer tube 10. The interior of the heat transfer tube 10 may be filled with a filler other than a resin. A filler having a higher heat conductivity than air is preferable. For example, metals, ceramics, and the like are also usable irrespective of their forms, including solid fillers (powders and pellets) and liquid fillers. A tube, one end of which is blocked, is also usable as the heat transfer tube 10.

According to the electric heater 1 having the above-described configuration, the heating part 25 is formed so as to extend along a part of the heat transfer tube 10 accommodating the heater body 20, and it is thus possible to create a desired temperature distribution in the longitudinal direction of the heat transfer tube 10, enabling topical heating of the heating target in an efficient manner. Moreover, the heat transfer tube 10 can be easily made longer by extending the lead part 26 connecting the heating part 25 to the outside of the heat transfer tube 10, and, accordingly, the electric heater 1 can be easily inserted into an injection needle or the like that has a small opening and a great depth, and it is thus possible to selectively heat only an affected site.

Figure 4:
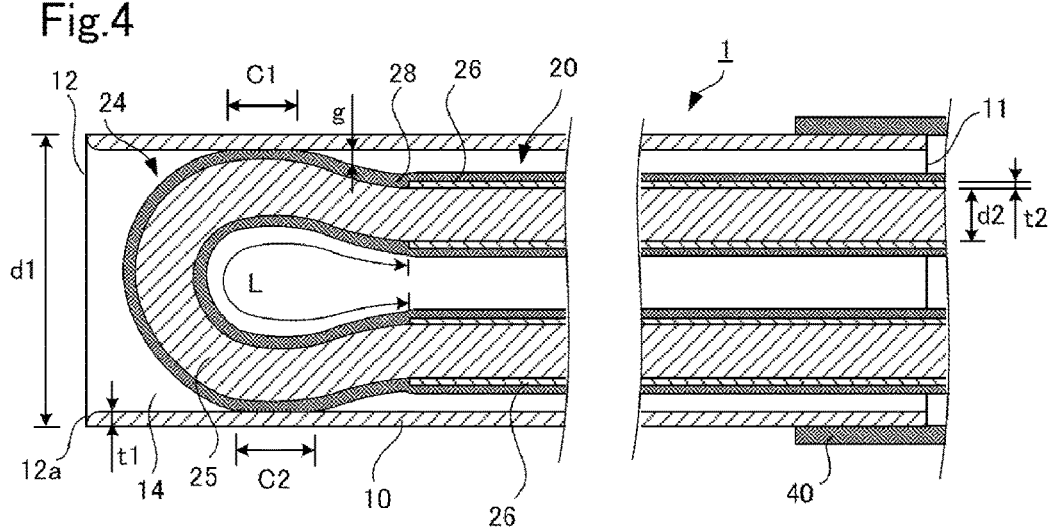
FIG. 4 is a cross-sectional view showing a modification of the electric heater shown in FIG. 3.

Although FIGS. 2 and 3 show one example of a configuration in which the heater body 20 is not in contact with the inner surface of the heat transfer tube 10 in the electric heater 1 of the present embodiment, it is preferable to adopt a configuration in which the heating part 25 of the heater body 20 is at least partially in contact with the inner surface of the heat transfer tube 10. FIG. 4 is a cross-sectional view showing one example of a configuration in which the heating part 25 is in contact with the inner surface of the heat exchanger tube 20.

In the electric heater 1 shown in FIG. 4, the radius of curvature when bending the heater body 20 at the heating part 25 to form the bent-back part 24 is large, and, accordingly, the heating part 25 is partially in contact with the inner circumferential surface of the heat transfer tube 10 via the jacket 28. According to the configuration shown in FIG. 4, the heating part 25 heats the heat transfer tube 10 without the intervention of the sealing resin 14, and, therefore, heat conductivity can be increased, and the heating target can be heated more efficiently. Moreover, since the heating part 25 is in contact with the heat transfer tube 10, the positional accuracy of the heating part 25 inside the heat transfer tube 10 can be increased, thus making it possible to suppress variations in heating performance from product to product and obtain a stable heating effect. It is preferable that the edge of the opening 12 of the heat transfer tube 10 is given rounding treatment (or chamfering treatment) 12a such that the heating part 25 having a large radius of curvature can be smoothly inserted into the heat transfer tube 10.

It is sufficient that the heating part 25 is at least partially in contact with the inner circumferential surface of the heat transfer tube 10. The heating part 25 and the heat transfer tube 10 may be in contact at one place but are preferably in contact at multiple places, and, accordingly, the heating part 25 can be easily retained in the heat transfer tube 10. Although it is preferable that the heating part 25 is in contact with both sides of the heat transfer tube 10 across the bent-back part 24, the heating part 25 may be in contact with other places of the heat transfer tube 10. It is preferable that the bent-back part 24 is formed in the heating part 25, and the heating part 25 can be easily brought into contact with the heat transfer tube 10 by taking advantage of the deformation of the heating part 25 for forming the bent-back part 24.

It is preferable that the length in the axial direction of the portion of the heating part 25 in contact with the heat transfer tube 10 is as large as possible in order to efficiently transfer heat to the heating target. Specifically, the ratio (C1+C2)/L of the total length (C1+C2) of the portions where the heating part 25 is in contact with the heat transfer tube 10 via the jacket 28 to the overall length L of the heating part 25 is preferably 0.1 to 1, more preferably 0.3 to 1, and even more preferably 0.5 to 1. The contact length of the heating part 25 and the heat transfer tube 10 can be measured using, for example, X rays. The overall length L of the heating part 25 in the axial direction is not particularly limited as long as the overall length L is determined in consideration of the size of a region to be heated. For example, the overall length L is about 1 to 30 mm.

As for the portion of the heating part 25 not in contact with the heat transfer tube 10, it is preferable that a gap g formed between the heating part 25 and the inner circumferential surface of the heat transfer tube 10 is as small as possible in order to suppress loss of heat to be transferred to the outside. For example, the average of the gap g is preferably 0 to 0.1 mm. The average of the gap g can be obtained from the arithmetic average of the shortest distance between the outer circumferential surface of the jacket 28 covering the heating part 25 and the inner circumferential surface of the heat transfer tube 10 in cross-sections obtained from 10 locations, which are spaced apart from each other at equal intervals, of the substantially entire heating part 25 excluding the bent-back part 24. The portion of the heating part 25 not in contact with the heat transfer tube 10 may be covered with a heat insulating material or the like in advance. When it is possible to ensure a sufficient contact length of the heating part 25 in contact with the heat transfer tube 10, a configuration can be adopted in which the heat transfer tube 10 is not filled with the sealing resin 14. When the average of the gap g is within the above numerical range, a configuration can also be adopted in which the heating part 25 is not in contact with the heat transfer tube 10 at all.

On the other hand, the gap formed between the lead part 26 and the inner circumferential surface of the heat transfer tube 10 is preferably as large as possible.

The heat transfer tube 10 may be partially filled with the sealing resin 14 to such an extent that the heating part 25 is covered, and a layer of air may surround the lead part 26. Since the heater body 20 produces heat mainly at the heating part 25, this configuration makes it possible to reduce the amount of the sealing resin 14 used, while maintaining good heating performance. An example of a method for filling only a part of the heat transfer tube 10 with the sealing resin 14 may be interposing an air-permeable mesh plate or the like between the heating part 25 and the lead part 26 and blocking the sealing resin 14 with the mesh plate when filling the heat transfer tube 10 with the sealing resin 14 by capillarity or pressure.

The heating part 25 may be formed from a shape-memory alloy, such as a nickel-titanium (Ni—Ti) alloy or an iron-manganese-silicon alloy, on which shape-memory heat treatment has been performed in advance such that the heating part 25 undergoes thermal deformation due to application of electricity or the like and is firmly attached to the inner circumferential surface of the heat transfer tube 10. Alternatively, the heating part 25 may be formed from a high-tension wire rod such as stainless-steel wire, piano wire, tungsten wire, or nichrome wire to configure the heating part 25 to be firmly attached to the heat transfer tube 10 due to elastic force exerted when bending the heating part 25. The tensile strength of the high-tension wire rod is preferably 800 MPa or greater. In this way, by forming the heating part 25 from a shape-memory alloy or a high-tension wire rod, at least a part of the heating part 25 can be firmly attached to the heat transfer tube 10 in an easy and reliable manner, and, also, the heating part 25 can be reliably retained at a desired place inside the heat transfer tube 10, thus making it possible to topically heat the heating target in an accurate manner.

In the configuration shown in FIG. 4, when an outer diameter d1 of the heat transfer tube 10 is excessively small, a suitable thickness of the linear body cannot be attained, thus making it difficult to ensure an insertion space for, and an amount of heat produced from, the heater body 20. On the other hand, when the outer diameter d1 is excessively large, the puncture needle for accommodating the heat transfer tube 10 is thick and is likely to cause pain and tissue destruction during puncturing. Therefore, the outer diameter d1 is preferably 0.2 to 0.7 mm, more preferably 0.3 to 0.6 mm, and even more preferably 0.3 to 0.5 mm. A smaller thickness t1 of the heat transfer tube 10 results in higher heat conduction efficiency and is thus preferable, but an excessively small thickness t1 makes it difficult to ensure sufficient strength against bending deformation or the like that occurs during puncturing. Therefore, the thickness t1 is, for example, about 0.01 to 0.26 mm and preferably 0.03 to 0.04 mm.

In the heater body 20, it is preferable that the linear body constituting the heating part 25 has high resistance, while it is preferable that the covering that covers the linear body to constitute the lead part 26 has low resistance. Specifically, where R1 and R2 represent the resistances per unit length of the linear body and the covering in the axial direction, respectively, the higher the ratio of these resistances (R1/R2) is, the more efficiently the heating part 25 can heat. A preferable ratio of resistances (R1/R2) is, for example, 20 or greater. For example, when the linear body is a wire rod that has a diameter of 100 μm and is composed of SUS304 (electrical resistivity: $7.92 \times 10^{-7}$ Ωm) and the covering is a plating film that has a thickness of 10 μm and is composed of copper (electrical resistivity: $1.68 \times 10^{-8}$ Ωm), the ratio of resistances (R1/R2) is about 20.7. Although there is no particular upper limit to the ratio of resistances (R1/R2), the upper limit is 50 from a practical viewpoint.

A smaller diameter d2 of the linear body constituting the heating part 25 makes insertion into the heat transfer tube 10 easier and thus makes it possible to further narrow the heat transfer tube 10. On the other hand, an excessively small diameter makes it difficult to ensure a necessary amount of produced heat. Therefore the diameter is preferably 0.01 to 0.3 mm, e.g., about 0.1 mm. A larger thickness t2 of the covering that covers the heating part 25 to constitute the lead part 26 results in a larger ratio of resistances (R1/R2) and makes it possible to increase heating efficiency. On the other hand, an excessively large thickness results in a thick heater body 20 and makes insertion into the heat transfer tube 10 difficult. Therefore, the thickness t2 is preferably 0.001 to 0.165 mm, e.g., 0.005 mm.

Although the first embodiment of the present invention has been described in detail above, the specific aspects of the present invention are not limited to the above embodiment, and the second embodiment of the present invention will now be described in detail below.

Figure 5:
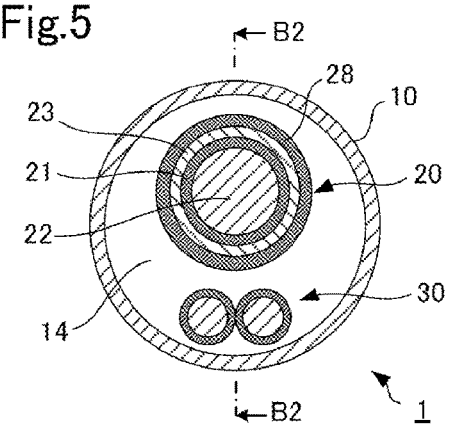
FIG. 5 is a transverse cross-sectional view of an electric heater according to the second embodiment of the present invention.
Figure 6:
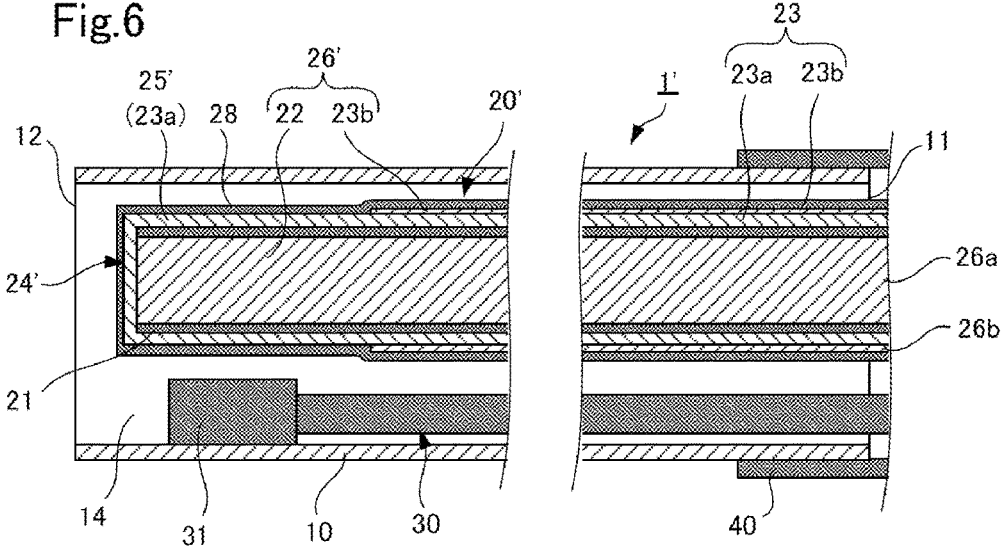
FIG. 6 is a cross-sectional view taken along the line B2-B2 of FIG. 5.

FIG. 5 is a transverse cross-sectional view of an electric heater 1' according to the second embodiment of the present invention. FIG. 6 is a cross-sectional view taken along the line B2-B2 of FIG. 5. In FIGS. 5 and 6, the same components as in FIGS. 2 and 3 are given the same reference numbers.

While the heater body 20 in which the heating part 25 and the lead part 26 are connected in the longitudinal direction is bent to form the bent-back part 24 in the first embodiment, it is also possible to configure the electric heater 1' using a heater body 20' in which an inner conductor 22 and an outer conductor 23 are coaxially disposed via an insulator 21, as in the second embodiment.

The heater body 20' as a whole has a linear form. The inner conductor 22 placed at the center is composed of a wire rod and can be formed from a metal material having a low electrical resistivity, such as gold, silver, copper, aluminum, and alloys thereof. In particular, it is preferable to form the inner conductor 22 from an "in-situ metal fiber reinforced copper alloy" reinforced with metal fiber during the process of wire rod formation, which can be processed into a fine wire having an extremely small diameter (e.g., about 0.03 mm) while maintaining good conductivity and durability. Although the inner conductor 22 is preferably a solid wire for providing a fine wire, the inner conductor 22 may be composed of a strand of multiple solid wires.

The insulator 21 can be formed from materials having high electrical insulation, such as fluororesins, olefin resins, polystyrene resins, polyester resins, polyurethane resins, polyimide resins, ABS resins, and the like. For example, polymer alloys of polyamide resins and ABS resins can be preferably used. Although the insulator 21 may be in the form of a tube that covers the inner conductor 22, the insulator 21 is preferably formed from a coating to have an extremely small thickness (e.g., about 0.04 mm).

The outer conductor 23 is provided over the entire outer circumferential surface of the insulator 21. It is preferable that the outer conductor 23 as well has a small thickness, and the outer conductor 23 can be formed from, for example, a metal plating film obtained by plating the insulator 21 with a metal material or a metal foil obtained by wrapping the insulator 21 with a metal material. The outer conductor 23 is entirely covered with the jacket 28 as in the first embodiment.

A heating part 25' is formed by configuring a part of the outer conductor 23 to be a high-resistance part 23a along the axial line of the heater body 20'. The portion other than the high-resistance part 23a (i.e., other than the heating part 25') in the outer conductor 23 is a low-resistance part 23b, and this low-resistance part 23b together with the inner conductor 22 constitutes a lead part 26'. The high-resistance part 23a is formed such that the electrical resistance per unit length along the axial line is greater than that of the low-resistance part 23b. When the high-resistance part 23a and the low-resistance part 23b are formed from the same metal material, the high-resistance part 23a is made thinner than the low-resistance part 23b. More specifically, by repeating metal plating on some parts of the insulator 21 to create a thickness distribution in the plating film or by varying the number of times the metal foil is wrapped around some parts of the insulator 21 to create a thickness distribution in the metal foil, the high-resistance part 23a and the low-resistance part 23b can be formed.

When the high-resistance part 23a and the low-resistance part 23b are formed from different metal materials, it is preferable that the electrical resistivity of the metal material of the high-resistance part 23a is higher than the electrical resistivity of the metal material of the low-resistance part 23b. For example, when gold, silver, copper, aluminum, an alloy thereof, or the like is used as the material of the low-resistance part 23b as with the inner conductor 22, nickel, iron, platinum, chromium, titanium, or an alloy thereof (such as stainless steel or nichrome) can be used as the material of the high-resistance part 23a.

Figure 7:
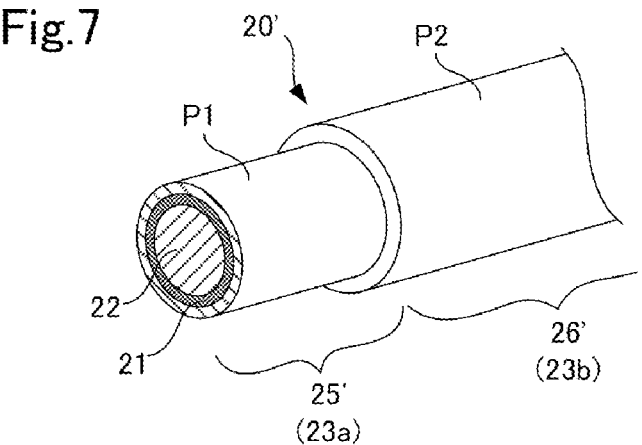
FIG. 7 is a perspective view schematically showing principal parts of the electric heater according to the second embodiment of the present invention.

Moreover, the high-resistance part 23a and the low-resistance part 23b may be formed using a combination of the aforementioned different thicknesses and different metal materials. For example, as schematically shown in FIG. 7, a high-resistance metal plating film P1 of a metal material having a high electrical resistivity, such as nickel, is formed over the entire outer circumferential surface of the insulator 21 covering the inner conductor 22 to form a linear body, and then the high-resistance metal plating film P1 is partially covered with a low-resistance metal plating film P2 of a metal material having a low electrical resistivity, such as copper. In this way, the low-resistance part 23b provided with the low-resistance metal plating film P2 constitutes the lead part 26', and the high-resistance part 23a where the high-resistance metal plating film P1 is exposed constitutes the heating part 25'. The exposed part of the high-resistance metal plating film P1 can be formed also by entirely covering the high-resistance metal plating film P1 with the low-resistance metal plating film P2 and then etching the low-resistance metal plating film P2. The heater body 20' having the configuration shown in FIG. 7 can be formed also by using metal foils in place of metal plating films, and can be easily produced by wrapping a high-resistance metal foil around the insulator 21 and then partially wrapping a low-resistance metal foil around the high-resistance metal foil. The lead part 26' can be formed also from a low-resistance metal wire other than the aforementioned plating film and metal foil. Examples of the metal wire include round wires, rectangular wires, and the like.

Although the heating part 25' is formed at the end of the outer conductor 23 in the present embodiment, the place where the heating part 25' is formed is not particularly limited so that the heating part 25' may be formed in the center of the outer conductor 23. Moreover, a plurality of heating parts 25' may be intermittently formed along the axial line of the heater body 20. Such heating parts 25' may be formed over the entire circumference at their respective places along the axial line or may be formed only partially in the circumferential direction. In the case of forming the heating parts 25' partially in the circumferential direction, the heating parts 25' may be a spiral plating film or the like, which makes it easy to ensure a necessary length of the heating parts 25 for heating the heating target.

The inner conductor 22 is conductive with the outer conductor 23 at the distal part, whereby a bent-back part 24' where the electrical path is bent back is formed. In the case of forming the heating part 25' from the high-resistance metal plating film P1, the bent-back part 24' can be formed by extending the high-resistance metal plating film P1 to the end face of the inner conductor 22. In addition, the inner conductor 22 and the outer conductor 23 can be made conductive by wire bonding, application of an electroconductive resin/electroconductive adhesive, or the like, or can be made conductive via through-holes formed in the insulator 21.

As in the first embodiment, the temperature sensor 30 is accommodated in the heat transfer tube 10, and a gap formed between the inner surface of the heat transfer tube 10 and the surfaces of the heater body 20' and the temperature sensor 30 is filled with the sealing resin 14. The temperature sensor 30 includes a temperature sensing part 31 at the distal end and is inserted into the heat transfer tube 10 through the opening 11 on the first-end side so that the temperature sensing part 31 is disposed near the heating part 25' of the heater body 20'. The proximal side of the temperature sensor 30 is connected to the connecting cord 42 inside the sleeve 40. It is preferable that the temperature sensing part 31 is in contact with the inner circumferential surface of the heat transfer tube 10 near the heating part 25'. According to this configuration, since the heat transfer tube 10 has good heat conductivity, a temperature close to the temperature of the heating target near the outer circumference of the heat transfer tube 10 can be measured, and, therefore, temperature control can be more precisely performed on the heating part 25'.

As with the electric heater 1 according to the first embodiment, since the heating part 25' is formed so as to extend along a part of the heat transfer tube 10 accommodating the heater body 20', the electric heater 1' having the above-described configuration can create a desired temperature distribution in the longitudinal direction of the heat transfer tube 10 and thus can topically heat the heating target in an efficient manner.

Moreover, by configuring the heater body 20' to include the coaxially disposed inner conductor 22 and outer conductor 23 such that a part of the outer conductor 23 is made into the high-resistance part 23a along the axial line to form the heating part 25', it is possible to make the heater body 20' compact and reduce the diameter of the electric heater 1' while enhancing the design flexibility of the heat transfer tube 10.

Moreover, since the outer conductor 23 constituting the lead part 26' can be formed from a metal plating film or a metal foil, the diameters of the heater body 20' and the electric heater 10 can be more easily reduced.

Since the heat transfer tube 10 has the openings 11 and 12 at the respective ends and is filled with the sealing resin 14, the space inside the heat transfer tube 10 can be easily sealed to prevent the entrance of foreign matter, and also the heating part 25' of the heater body 20' and the temperature sensing part 31 of the temperature sensor 30 can be reliably fixed to the desired places. Moreover, the use of a material having good heat conductivity as the sealing resin 14 makes it possible to efficiently heat the heating target. It is also possible to fill the heat transfer tube 10 with a filler other than a resin as stated above.

Figure 8:
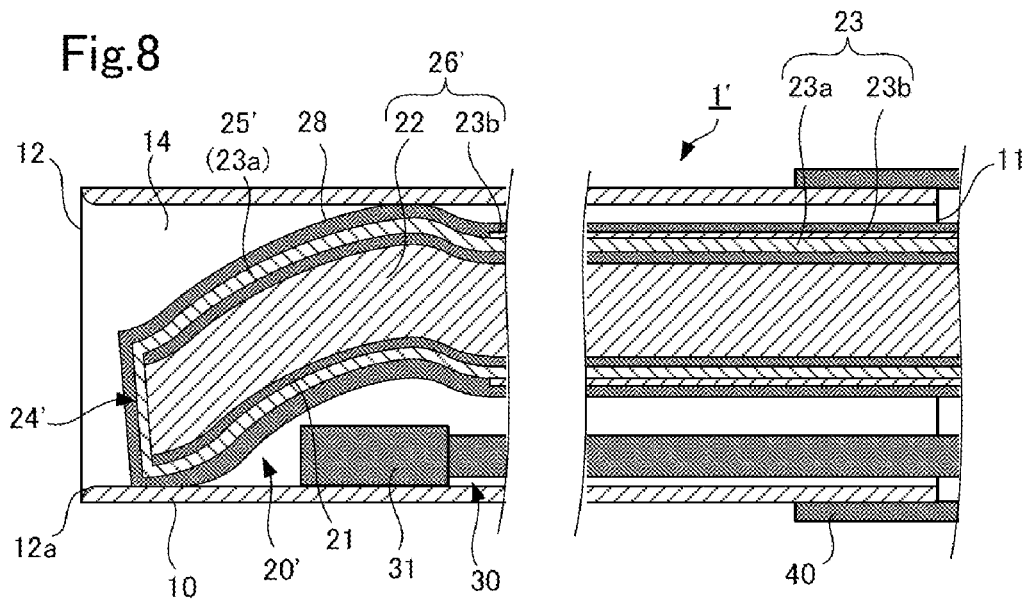
FIG. 8 is a cross-sectional view showing a modification of the electric heater shown in FIG. 6.

As shown in FIG. 8, the electric heater 1' of the second embodiment can also be configured such that the heating part 25' is in contact with the inner circumferential surface of the heat transfer tube 10. In the heater body 20' shown in FIG. 8, the heating part 25' is bend to cause both the proximal side and the distal side of the heating part 25' to be in contact with the inner circumferential surface of the heat transfer tube 10, and the heating part 25' is thus positioned and retained inside the heat transfer tube 10. In the configuration shown in FIG. 8 as well, it is preferable to use a shape-memory alloy or a high-tension wire rod as the material of the inner conductor 22 and the outer conductor 23. The dimensions of each component described for the electric heater 1 shown in FIG. 4 is also applicable to the similarly configured electric heater 1' shown in FIG. 8.

Figure 9:
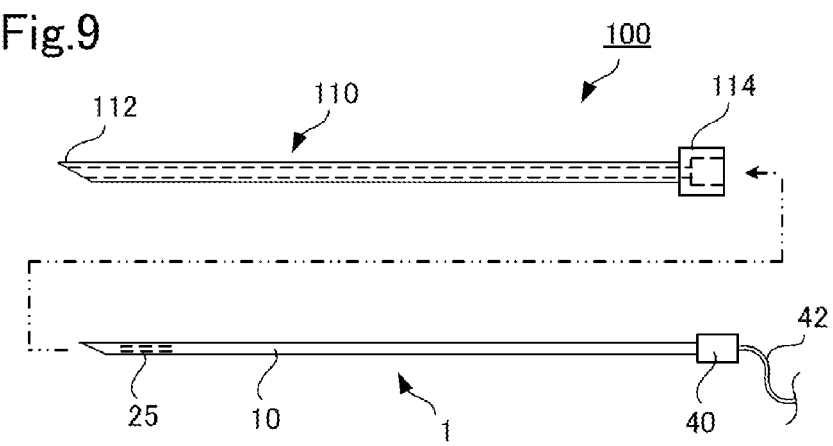
FIG. 9 is an exploded perspective view showing one embodiment of the electric heater of the present invention applied to a living body treatment instrument.

The application of the electric heater of the present invention is not particularly limited, and since a diameter reduction is easily achieved, the electric heater is particularly suitable for insertion into a small space that is extremely narrow and is elongated. FIG. 9 is an exploded cross-sectional view showing, as a preferable usage of the electric heater of the present invention, one embodiment in which the electric heater of the present invention is applied to a living body heating instrument for heating an affected site in a living body. A living body heating instrument 100 shown in FIG. 9 comprises a hollow puncture needle 110 having a puncturing part 112 at the distal end and an opening at each end, and the electric heater 1 removably inserted into the puncture needle 110. In the electric heater 1, the heater body is accommodated in the interior of the heat transfer tube 10. A detailed description of the structure thereof is omitted since the structure is identical to the electric heaters 1 and 1' of the first and second embodiments.

The resin-filled distal part of the heat transfer tube 10 is tapered in accordance with the shape of the puncturing part 112 of the puncture needle 110 and is polished. The sleeve 40 provided on the proximal side of the heat transfer tube 10 is attachable to an attachment part 114 provided on the proximal side of the puncture needle 110, and by inserting the heat transfer tube 10 into the puncture needle 110, the electric heater 1 is positioned in and fixed to the puncture needle 110. The heating part 25 of the electric heater 1 is provided so as to be placed near the puncturing part 112 when the electric heater 1 is inserted into the puncture needle 110. Although the dimensions of the puncture needle 110 are not particularly limited, for example, the inner diameter is about 0.4 mm, and the length is about 150 mm. The thickness and the length of the electric heater 1 are set such that the electric heater 1 can be inserted into the hollow part of the puncture needle 110 having such dimensions.

By puncturing a living body of a human, an animal, or the like with the puncture needle 110 to which the electric heater 1 is attached, the living body heating instrument 100 having the above-described configuration can selectively heat only a diseased site such as cancer cells without adversely affecting healthy sites, and thus an effective treatment can be performed. Although the temperature of heating by the electric heater 1 is not particularly limited, the surface temperature of the heat transfer tube 10 near the heating part 25 is preferably about 50 to 60° C. After cauterization treatment, withdrawing only the electric heater 1, with the puncture needle 110 still puncturing the living body, enables a pharmaceutical agent or the like to be supplied to the diseased site from the distal part 112 of the puncture needle 110. In order to prevent attachment of bodily fluid such as blood to the inner surface of the puncture needle 110 after withdrawal of the electric heater 1, it is preferable to perform water-repelling treatment or the like in advance on the inner surface of the puncture needle 110 and the outer surface of the heat transfer tube 10. Instead of inserting the electric heater 1 into the puncture needle 110 as described above, forming the distal part of the heat transfer tube 10 into a sharp-edged needle makes it possible to use the electric heater 1 itself also as a puncture needle.

REFERENCE SIGNS LIST

1 Electric heater
10 Heat transfer tube
11, 12 Openings
14 Sealing resin
20 Heater body
21 Insulator
22 Inner conductor
23 Outer conductor
23*a* High-resistance part
23*b* Low-resistance part
24 Bent-back part
25 Heating part
26 Lead part
26*a*, 26*b* Ends
28 Jacket
30 Temperature sensor
31 Temperature sensing part

The invention claimed is:

1. An electric heater comprising:
a heat transfer tube that has a hollow space inside the heat transfer tube, having distal and proximal ends in an axial direction of the heat transfer tube, each of the ends having an opening;
a heater body that is accommodated in the heat transfer tube, being formed with three parts that are an inner conductor, an outer conductor and a bent-back part,
a sealing resin that entirely fills a remaining of the hollow space, the remaining being defined as a space that is inside the heat transfer tube and not occupied with the heater body, wherein
these three parts are made of a main metal having a predetermined electrical resistivity,
the inner and outer conductors are coaxially disposed such that the inner conductor is inside the outer conductor, extending along to the axial direction of the heat transfer tube such that each of the conductors has distal and proximal ends in the axial direction, and an insulator intervening between the inner and outer conductors,
the distal ends of the conductors are connected with the bent-back part, and the bent-back part is positioned at a side of the distal end of the heat transfer tube, and the proximal ends of the conductors are positioned at the proximal end of the heat transfer tube such that these proximal ends of the conductors are exposed outside the heat transfer tube,
the outer conductor is further segmented into a heating part and a leading part,
the leading part extending from the proximal end toward the distal end of the heat transfer tube, and an outer surface of the leading part being covered by a cover metal that has an electrical resistivity lower than the electrical resistivity of the main metal,
the heating part being positioned closer to the distal end of the heat transfer tube than the leading part, and an outer surface of the heating part being not covered with the cover metal such that a resistance of the leading part per unit length is lower than that of the heating part, and that the heating part generates heat and conveys the heat toward the heat transfer tube when the heater body is electrified.

2. The electric heater according to claim 1, wherein the bent-back part is not covered with the cover metal.

3. The electric heater according to claim 1, wherein an outer surface of the heating part is covered with a jacket, and
a portion of the jacket is in contact with an inner circumferential surface of the heat transfer tube.

4. The electric heater according to claim 3, wherein a ratio of a length in an axial direction of a portion of the heating part in contact with the heat transfer tube to a total length of the heating part is 0.1 to 1.

5. The electric heater according to claim 3, wherein another portion of the jacket, which is different from the portion of the jacket in contact, is in contact with the inner circumferential surface of the heat transfer tube.

6. The electric heater according to claim 1, wherein the heating part is composed of a shape-memory alloy or a high-tension wire rod.

7. The electric heater according to claim 1, wherein the sealing resin is an epoxy resin.

8. The electric heater according to claim 1, wherein the heat transfer tube has an outer diameter of 0.2 to 0.7 mm.

9. The electric heater according to claim 1, wherein a gap formed between the heating part and the heat transfer tube has an average of 0 to 0.1 mm.

10. The electric heater according to claim 1, wherein a ratio of resistances (R1/R2) is 20 or greater where R1 and R2 respectively represent resistances of the outer conductor and the cover metal per unit lenth in the axail direction.

11. The electric heater according to claim 1, further comprising
a temperature sensor for sensing a temperature near the heating part inside the heat transfer tube, wherein
a temperature sensing part of the temperature sensor is in contact with an inner circumferential surface of the heat transfer tube.

12. A method for manufacturing the electric heater of claim 1, comprising:
a first step of producing the heater body by partially covering a surface of the heater body composed of a high-resistance metal material with a low-resistance metal material having a lower electrical resistivity than the material of the heater body and forming the bent-back part in the linear body;
a second step of accommodating the heater body in the heat transfer tube,
a third step of filling the hollow space of the heat transfer tube with the sealing resin that is entered from one of the openings of the heat transfer tube,
wherein a portion where the conductors are covered with the low-resistance metal material constitute the leading part, and a portion where the linear bodies is exposed constitutes the heating part.

13. The electric heater manufacturing method according to claim 12, wherein
the heating part is formed from a high-tension wire rod and covered with a jacket; and
the second step comprises firmly attaching the heating part to an inner circumferential surface of the heat transfer tube via the jacket by elastic force exerted when bending the heating part.

14. The electric heater manufacturing method according to claim 12, wherein
the heating part is formed from a shape-memory alloy and covered with a jacket; and
the second step comprises firmly attaching the heating part to an inner circumferential surface of the heat transfer tube via the jacket by thermally deforming the heating part after the heating part is accommodated in the heat transfer tube.

15. An electric heater comprising:
a heat transfer tube that has a hollow space inside the heat transfer tube, having distal and proximal ends in an axial direction of the heat transfer tube, each of the ends having an opening;
a heater body that is accommodated in the heat transfer tube, being formed with three parts that are a first linear body, a second linear body and a bent-back part,
a sealing resin that entirely fills a remaining of the hollow space, the remaining being defined as a space that is inside the heat transfer tube and not occupied with the heater body, wherein
these three parts are made of a main metal having a predetermined electrical resistivity,
the first and second linear bodies are arranged in parallel extending along to the axial direction of the heat transfer tube, in a physically separated fashion, such that each of the linear bodies has distal and proximal ends in the axial direction,
the distal ends of the first and second linear bodies are connected with the bent-back part, and the bent-back part is positioned at a side of the distal end of the heat transfer tube, and the proximal ends of the first and second linear bodies are positioned at the proximal end of the tube such that these proximal ends of the linear bodies are exposed outside the heat transfer tube,
each of the first and second linear bodies is further segmented into a heating part and a leading part,
the leading part extending from the proximal end toward the distal end of the tube, and an outer surface of the leading part being covered by a cover metal that has an electrical resistivity lower than the electrical resistivity of the main metal,
the heating part being positioned closer to the distal end of the tube than the leading part, and an outer surface of the heating part being not covered with the cover metal such that a resistance of the leading part per unit length is lower than that of the heating part, and that the heating part generates heat and conveys the heat toward the tube when the heater body is electrified.

16. The electric heater according to claim 15, wherein
the heating part of the first linear body contacts to an inner circumferential surface of the heat transfer tube at a first contact point,
the heating part of the second linear body contacts to the inner circumferential surface of the heat transfer tube at a second contact point,
the first and second contact points are positioned opposite with respect to a diameter direction of the heat transfer tube in order to be separated by the same distance as an inner diameter of the heat transfer tube.

17. The electric heater according to claim 15, wherein
a ratio of resistances (R1/R2) is 20 or greater where R1 and R2 respectively represent a resistance of the first and second linear bodies and a resistance of the cover metal per unit length in the axial direction.

* * * * *